US008283113B2

(12) United States Patent
Dmitrovsky et al.

(10) Patent No.: US 8,283,113 B2
(45) Date of Patent: Oct. 9, 2012

(54) COMPOSITIONS AND METHODS FOR PREVENTING AND TREATING CANCER VIA MODULATING UBE1L, ISG15 AND/OR UBP43

(75) Inventors: Ethan Dmitrovsky, Hanover, NH (US); Bret A. Hassel, Woodbine, MD (US); Sutisak Kitareewan, Subhanburi (TH); Ian Pitha-Rowe, Baltimore, MD (US)

(73) Assignee: Trustees of Dartmouth College, Hanover, NH (US)

( * ) Notice: Subject to any disclaimer, the term of this patent is extended or adjusted under 35 U.S.C. 154(b) by 81 days.

(21) Appl. No.: 12/262,337

(22) Filed: Oct. 31, 2008

(65) Prior Publication Data
US 2009/0131357 A1    May 21, 2009

Related U.S. Application Data

(63) Continuation-in-part of application No. 10/506,226, filed on Dec. 29, 2004, now abandoned.

(51) Int. Cl.
*C12Q 1/00* (2006.01)
(52) U.S. Cl. ............................................................ 435/4
(58) Field of Classification Search ........................ None
See application file for complete search history.

(56) References Cited

U.S. PATENT DOCUMENTS 6,329,171 B1 * 12/2001 Kapeller-Libermann ... 435/69.1

OTHER PUBLICATIONS

By Montero et al. (Cancer Research, 1999, 59: 5286-5293).*
Hetherington et al (Blood, 96(11) pt1: 19a).*
Liu et al (Molecular and Cellular Biology, Apr. 1999, 19(4): 3029-3038).*
Montero et al. (Cancer Research, 1999, 59: 5286-5293).*
Hetherington et al (Blood, 96(11) pt1: 19a.*
Gura (Science, 1997, 278:1041-1042.).*
Tamayo et al., "Interpreting patterns of gene expression with self-organizing maps:Methods and application to hematopoietic differentiation", 1999 Proc Natl Acad Sci USA 96:2907-2912.
Yoshida et al., "Accelerated degradation of PML-retinoic acid receptor α (PML-RARA) oncoprotein by all-trans-retinoic acid in acute promyelocytic leukemia:possible role of the proteasome pathway", 1996 Cancer Res 56:2945-2948.
Raelson et al., "The PML/RARα oncoprotein is a direct molecular target of retinoic acid in acute promyelocytic leukemia cells", 1996 Blood 88:2826-2832.
Nervi et al., "Caspases mediate retinoic acid-induced degradation of the acute promyelocytic leukemia PML/RARα fusion protein", 1998 Blood 92:2244-2251.
Zhu et al., "Retinoic acid induces proteasome-dependent degradation of tetinoic acid receptor α (RARα) and oncogenic RARα fusion proteins", 1999 Proc Natl Acad Sci USA 96:14807-14812.
Yuan & Krug, "Influenza B virus NS1 protein inhibits conjugation of the interferon (IFN)-induced ubiquitin-like ISG15 protein", 2001 EMBO J 20:362-371.
Kok et al., "A gene in the chromosomal region 3p21 with greatly reduced expression in lung cancer is similar to the gene for ubiquitin-activating enzyme", 1993 Proc Natl Acad Sci USA 90:6071-6075.
Carritt et al., "A gene from human chromosome region 3p21 with reduced expression in small cell lung cancer", 1992 Canceer Res 52 :1536-1541.
McLaughlin et al., "The ubiquitin-activating enzyme E1-like protein in lung cancer cell lines", 2000 Int J Cancer 85 :871-876.
Isoe et al., "Inhibition of different steps of the ubiquitin system by cisplatin and aclarubicin", Biochimica et Biophysica Acta 1992 1117:131-135.
Malakhova et al., "LPS stimulates a novel ubiquitin protease expression in monocytic cells", Blood 2000 96(11):Part 1, p. 19a (abstract #67).
Abato et al., "Combinatorial library of serine and cysteine protease inhibitors that interact with both the S and S' binding sites", J Med Chem 1999 42(19):4001-4009.
Demarcus et al., "Small ring constrained peptidomimetics. Synthesis of epoxy peptidomimetics, inhibitors of cysteine proteases", J Org Chem 2001 66(3):697-706.
Baek et al. 1997 J. Biol. Chem. 272:25560-25565.
Montero et al Cancer Research, 59:5286-5293.
Hetherington et al. (Blood, 2000, 96(11) pt1: 19a, abstract # 67—I. D.S.).
Lu et al (BMC Cell Biology, Aug. 20, 2002).
Tokarz et al (JBC, Nov. 2004, 279(45):46424-46430).

* cited by examiner

*Primary Examiner* — Sean Aeder
(74) *Attorney, Agent, or Firm* — Licata & Tyrrell P.C.

(57) ABSTRACT

Compositions and methods of using compositions that induce UBE1L or a ubiquitin-like protein ISG15, or inhibit a deconjugase UBP43 to degrade oncogenic proteins and enhance apoptosis of cancer (neoplastic) or pre-cancerous (pre-neoplastic) cells are provided. Methods for the prevention or treatment of cancer via administration of these compositions are also provided.

1 Claim, 1 Drawing Sheet

US 8,283,113 B2

COMPOSITIONS AND METHODS FOR PREVENTING AND TREATING CANCER VIA MODULATING UBE1L, ISG15 AND/OR UBP43

This application is a continuation-in-part of U.S. patent application Ser. No. 10/506,226, filed Dec. 29, 2004 now abandoned, which claims benefit of PCT/US2003/006905, filed Mar. 5, 2003, which claims the benefit of U.S. Provisional Application No. 60/361,830, filed Mar. 5, 2002, the contents of which are incorporated herein by reference in their entireties.

This invention was made with government support under Grant Nos. RO-1-CA62275 and RO-1-CA87546 awarded by the National Institutes of Health. The government has certain rights in the invention.

BACKGROUND OF THE INVENTION

Acute promyelocytic leukemia (APL) (FAB M3) cases express the oncogenic product of the t(15; 17) chromosomal rearrangement, promyelocytic leukemia (PML)/retinoic acid receptor α (RAR α) (Nason-Burchenal, et al. (1996) In *Molecular Biology of Cancer*, ed. Bertino, Academic San Diego, 1st Ed., pp 1547-1560; Nason-Burchenal & Dmitrovsky (1999) In *Retinoids: The Biochemical and Molecular Basis of Vitamin A and Retinoid Action*, eds. Nau & Blaneer, Springer, Berlin, pp. 301-322). All-trans-retinoic acid (RA) treatment causes complete remissions in these APL cases through induction of leukemic cell differentiation (Nason-Burchenal et al. (1996) supra; Nason-Burchenal & Dmitrovsky (1999) supra). A hallmark of RA response in APL is PML/RARα degradation that reverses PML/RARα oncogenic effects (Kakizuka, et al. (1991) *Cell* 68:663-674; Yoshida, et al. (1996) *Cancer Res.* 56:2945-2948; Raelson, et al. (1996) *Blood* 88:2826-2832; Nervi, et al. (1998) *Blood* 92:2244-2251; Zhu, et al. (1999) *Proc. Natl. Acad. Sci. USA* 96:14807-14812). Proteasomal inhibitors prevent PML/RARα proteolysis, despite RA treatment, which is indicative of a proteasome-dependent pathway in this degradation (Yoshida, et al. (1996) supra; Raelson, et al. (1996) supra; Nervi et al. (1998) supra; Zhu, et al. (1999) supra). PML/RARα expression results in dominant-negative transcriptional repression (Kakizuka, et al. (1991) supra; de The, et al. (1991) *Cell* 68:675-684). This repression is antagonized by pharmacological RA dosages that overcome inhibitory effects on transcription of the N-Cor/SMRT corepressor complex that has histone deacetylase activity (Lin, et al. (1998) *Nature* (London) 391:811-814; Grignani, et al. (1998) *Nature* (London) 391:815-818). RA treatment recruits a coactivator complex that stimulates transcription, resulting in activation of target genes (Lin, et al. (1998) supra; Grignani, et al. (1998) supra).

To understand the molecular basis of RA response in APL, RA target gene identification has been sought. GOS2 has been suggested as a putative RA target gene as determined by microarray analysis of APL cells (Tamayo, et al. (1999) *Proc. Natl. Acad. Sci. USA* 96:2907-2912). The precise function of GOS2 is not yet known, but it was first identified as regulated during the cell cycle (Russell & Forsdyke (1991) *DNA Cell Biol.* 10:581-591), suggesting a role in cell cycle control.

Another candidate retinoid target gene is the CCAAT/enhancer binding protein epsilon (C/EBP epsilon) that contributes to retinoid transcriptional effects in APL (Park, et al. (1999) *J. Clin. Invest.* 103:1399-1408). However, this species has not been linked to the degradation of PML/RARα.

Recent microarray analysis of RA-treated NB4 APL cells reported the prominent induction of UBE1L (ubiquitin-activating enzyme E1-like) (Tamayo, et al. (1999) supra). The proteasome-dependent degradation of PML/RARα has also been proposed as a mechanism by which RA overcomes PML/RARα oncogenic effects (Yoshida, et al. (1996) supra; Raelson, et al. (1996) supra; Nervi, et al. (1998) supra; Zhu, et al. (1999) supra). Hammerhead ribozymes that target PML/RARα have been used to show how PML/RARα degradation signals apoptosis but not differentiation in transfected APL cells that are either RA-sensitive or RA-resistant (Nason-Burchanel, et al. (1998) *Blood* 92:1758-1767; Nason-Burchanel, et al. (1998) *Oncogene* 17:1759-1768).

SUMMARY OF THE INVENTION

The present invention features a method for identifying agents as potential therapeutics against cancer by determining the ability of the agent to induce UBE1L and/or ubiquitin proteins such as ISG15 or determining the ability of the agent to inhibit the deconjugase UBP43.

The present invention also features a method for enhancing pro-apoptotic and degradative pathways of neoplastic (cancerous) cells or pre-neoplastic (pre-cancerous) cells with an agent that induces UBE1L and/or ubiquitin-like proteins such as ISG15 or an agent which inhibits the deconjugase UBP43.

Another feature of the present invention is to provide a method for preventing or treating cancer in a patient which comprises administering to a patient an agent which induces UBE1L and/or ubiquitin-like proteins such as ISG15 or an agent which inhibits UBP43.

DETAILED DESCRIPTION OF THE INVENTION

Figure 1:
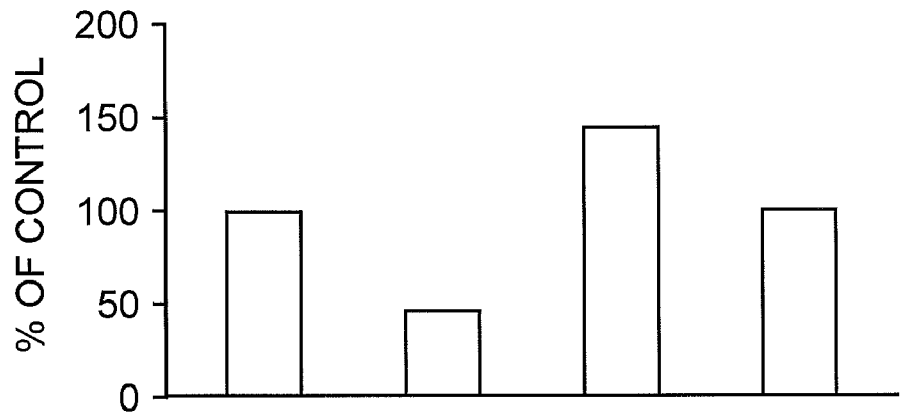
FIG. 1 shows the effect of UBE1L or UBP43 cotransfection on UBE1L-mediated inhibition of cyclin D1. UBP43 antagonized UBE1L-mediated inhibition of cyclin D1 while having no appreciable effect on actin expression. Quantification of signals is provided.

It has now been found that UBE1L and the UBE1L-dependent pathway suppress cancer growth. For example, UBE1L is the retinoid target gene in APL that antagonizes PML/RARα oncogenic effects by triggering PML/RARα degradation. The consequence of this action is the promotion of apoptosis resulting in anti-oncogenic effects of UBE1L in APL and other neoplastic or pre-neoplastic cell contexts, including lung cancer. Accordingly, compositions which target UBE1L or UBE1L-dependent pathway proteins such as the ubiquitin-like protein ISG15 or the deconjugase UBP43, find application in preventing and treating cancer.

Thus, the present invention features anticancer agents, methods for designing or screening for new anticancer agents and methods for using such agents in the prevention or treatment of cancer. In one embodiment, agents of the invention induce the activity and/or expression ubiquitin-activating enzyme E1-like protein (UBE1L). In another embodiment, agents of the invention induce the activity and/or expression of ubiquitin-like proteins such as ISG15. In an alternative embodiment, agents of the invention inhibit the activity and/or or expression of the deconjugase UBP43. By inducing the expression and/or activity of UBE1L or ISG15, or inhibiting the expression and/or activity of UBP43, pro-apoptotic and degradative pathways of neoplastic cells or pre-neoplastic cells are activated. In this regard, agents of the present invention are useful in preventing or treating cancerous or neoplastic as well as pre-cancerous or pre-neoplastic cells.

UBE1L is widely expressed in diverse human tissues and tumor cell lines. UBE1L acts as the activating enzyme for the ubiquitin-like protein ISG15. As demonstrated herein, UBE1L is a RA-inducible gene target in acute promyelocytic leukemia and U937 and THP1 cells, implicating a broad biological role for UBE1L. Expression of ISG15 as well as the deconjugase UBP43 have also been found to be induced by RA and appear to be regulated in a coordinated fashion with UBE1L. As shown herein, this induction occurs only in RA-sensitive cells, and not in RA-insensitive cells. Further, coordinate regulation and physical association of UBE1L and ISG15 induces degradation of oncogenic proteins including, but not limited to, PML/RARα, cyclin D1, and PML, in RA-sensitive cells. In addition, the induction of degradation of these oncogenic proteins by UBE1L and ISG15 appears to preferentially trigger apoptosis. PML/RARα degradation is inhibited by UBP43 transfection.

Similar analysis was conducted in lung cancer cells. In this analysis, UBE1L transduction was found to suppress cyclin D1 expression and growth of HBE and lung cancer cells. Transfection of the UBE1L-ISG15 deconjugase, ubiquitin specific protein 18 (UBP43), antagonized UBE1L-dependent inhibition of cyclin D1 and ISG15-cyclin D1 conjugation. In contrast, UBE1L knockdown increased cyclin D1 expression. Moreover, UBE1L conferred growth suppression by preferentially targeting cyclin D1. These findings demonstrate the role of UBE1L and UBE1L-dependent pathway proteins (i.e., ISG15 and UBP43) in growth suppression by targeting cyclin D1 for repression.

Accordingly, agents that induce activity and/or expression of UBE1L or ubiquitin-like proteins such as ISG15 and agents that inhibit activity and/or expression of the deconjugase UBP43 are expected to be useful in treatment of neoplasia and pre-neoplasia, particularly RA-sensitive cancers and cancers expressing oncogenic proteins such PML/RARα. Cancers of particular relevance include, breast cancer, APL, lung cancer, T-cell lymphoma, ovarian cancer, gastric cancer.

Agents that selectively induce UBE1L or ISG15 expression or activity, or inhibit the expression or activity of UBP43 in APL are expected to cause anti-leukemic effects by triggering PML/RARα degradation and apoptosis. Based on findings presented here and previous reports (Yuan & Krug (2001) *EMBO J.* 20:362-371), UBE1L is also expected to have an important biological role beyond APL. UBE1L maps to chromosome 3p, a region frequently deleted in lung cancers; UBE1L repression is frequent in lung cancers (Kok, et al. (1993) *Proc. Natl. Acad. Sci. USA* 90:6071-6075; Carritt, et al. (1992) *Cancer Res.* 52:1536-1541), where it may exert a tumor suppressive effect. When coupled with the expression pattern of UBE1L in human tissues or tumor cells (McLaughlin, et al. (2000) *Int. J. Cancer* 85:871-876) and the results reported herein, UBE1L and the UBE1L-dependent pathway (i.e., ISG15 and UBP43) regulate growth of both normal and neoplastic or pre-neoplastic cells.

Cancer cells, and in particular RA-sensitive cancer cells or cancer cells expressing oncogenic proteins such as PML/RARα can be contacted with agents of the present invention that induce UBE1L or ISG15 expression or activity, or inhibit the expression or activity of the deconjugase UBP43 to trigger degradation of oncogenic proteins such as PML/RARα and apoptosis in the cancer cells. Activation of this newly identified pathway is also expected to trigger degradation of other oncogenic proteins in non-leukemia, including other neoplastic or pre-neoplastic cells such as lung and breast cancer cells. In particular embodiments, agents of this invention selectively induce UBE1L or ISG15 activity or expression, or selectively inhibit UBP43 activity or expression.

As used herein, a selective agent is any molecular species that is an UBE1L or ISG15 activator or UBP43 inhibitor but which fails to activate or inhibit, or activates or inhibits to a substantially lesser degree the expression or activity of other any other protein in the cell. In this regard, selectivity of agents of the invention should alleviate undesirable clinical toxicities that complicate RA or arsenic trioxide treatments. Methods for assessing the selectively of agents are known in the art and can be based upon any conventional assay including, but not limited to the determination of the half maximal (50%) inhibitory concentration (IC) of a substance (i.e., 50% IC, or $IC_{50}$), the binding affinity of the molecule, and/or the half maximal effective concentration ($EC_{50}$). UBE1L, ISG15 and UBP43 nucleic acids and proteins that can be employed in such assays are well-known in the art and respectively set forth, e.g., in GENBANK Accession Nos. NM_003335 and NP_003326 (human UBE1L or ubiquitin-like modifier activating enzyme 7, UBA7); NM_005101 and NP_005092 (human ISG15); and NM_017414 and NP_059110 (human UBP43 or ubiquitin specific peptidase 18, USP18).

Selective activators of UBE1L or ISG15 expression or activity include, but are not limited to nucleic acids encoding UBE1L (e.g., GENBANK Accession No. NM_003335) or ISG15 (e.g., GENBANK Accession No. NM_005101). These nucleic acid molecules can be used as is (e.g., as naked DNA) or via vectors (e.g., a plasmid or viral vector such as an adenoviral, lentiviral, retroviral, adeno-associated viral vector or the like) harboring nucleic acids encoding the UBE1L and/or ISG15. Desirably, a vector used in accordance with the invention provides all the necessary control sequences to facilitate expression of UBE1L and/or ISG15. Such expression control sequences can include but are not limited to promoter sequences, enhancer sequences, etc. Such expression control sequences, vectors and the like are well-known and routinely employed by those skilled in the art.

Selective inhibitors of UBP43 expression include, but are not limited to, agents such as microRNA, shRNA, siRNA, antisense, or ribozyme molecules specifically targeted to a nucleic acid molecule encoding UBP43 (e.g., GENBANK Accession No. NM_017414). Such agents can be designed based upon routine guidelines well-known to those skilled in the art. For example, siRNA target sites in a gene of interest can be 19-27 nucleotides in length, include an AA dinucleotide sequence at the 5' end and preferably have a G/C content of 30-50% (see, e.g., Elbashir, et al. (2001) *Nature* 411: 494-498). Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art. An exemplary siRNA targeting human UBP43 is, e.g., 5'-gat ccc cag gag aag cat tgt ttt caa att caa gag att tga aaa caa tgc ttc tcc ttt ttt a-3' (SEQ ID NO:1) and 5'-agc tta aaa aag gag aag cat tgt ttt caa atc tct tga att tga aaa caa tgc ttc tcc tgg g-3' (SEQ ID NO:2)(Malakhova, et al. (2006) *EMBO J.* 25(11): 2358-2367).

Selective inhibitors of UBP43 activity can be based upon the UBP43 substrate Leu-Arg-Gly-Gly-Met-His-Ile-Ser (SEQ ID NO:3) (Malakhov, et al. (2002) *J. Biol. Chem.* 277: 9976-9981). See, e.g., Kim ((1999) *Biopolymeers (Peptide Science)* 51:3-8) who teaches the design of protease inhibitors on the basis of substrate stereospecificity. Other selective inhibitors can be derived from ubiquitin aldehyde, an inhibitor of ubiquitin-specific processing protease (UBP) family of deubiquitinating enzymes (Hu, et al. (2002) *Cell* 111:1041-1054), or N-ethylmaleimide, a general inhibitor of cysteine proteinases.

In addition to the above-referenced activators and inhibitors, it is contemplated that any conventional screening assay can be employed for identifying or selecting additional or more selective activators or inhibitors, or derivatives or analogs of known activators or inhibitors for UBE1L, ISG15, or UBP43. Screening, in accordance with the present invention, involves determining an agent's ability to induce UBE1L or ISG15 expression or activity, or to inhibit UBP43 expression or activity. An increase or decrease in the expression of a protein of this invention can be determined by contacting a cell expressing said protein with a test agent, and measuring whether the agent increases or decreases the amount of mRNA encoding the protein (e.g., by northern blot analysis or RT-PCR) or amount of protein (e.g., by western blot or dot blot analysis) in the cell. An increase or decrease in the activity of a protein of this invention can be determined by contacting the protein or a cell expressing said protein with a test agent, and measuring whether the agent increases or decreases the activity of the protein (e.g., in an in vitro assay or based upon the expression of a downstream protein). For example, it can be determined whether cyclin D1 expression is altered by the agent. By way of further illustration, an in vitro protease assay can be conducted with UBP43 and a substrate disclosed herein. Agents which increase the level of UBE1L or ISG15 mRNA or protein in the presence of a test agent as compared to UBE1L or ISG15 mRNA or protein levels in the absence of the test agent is indicative of the test agent inducing UBE1L or ISG15 and being potentially useful as an anticancer agent. Similarly, agents that inhibit the expression or deconjugase activity of UBP43 as compared to UBP43 expression or activity in the absence of the test agent is indicative of a test agent inhibiting UBP43 and being potentially useful as an anticancer agent. Such agents can then be administered to prevent and treat cancer.

Agents can be identified and obtained from libraries of compounds containing pure agents or collections of agent mixtures. Examples of pure agents include, but are not limited to, proteins, peptides, nucleic acids, oligonucleotides, carbohydrates, lipids, synthetic or semisynthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained. An exemplary library of cysteine peptidase inhibitors to screen and identify UBP43 inhibitors are disclosed by Abato et al. ((1999) *J. Med. Chem.* 42(19):4001-9). These inhibitors are based upon a cyclohexanone nucleus and are designed to probe binding interactions in the S2 and S2' binding sites. Moreover, Damarcus et al. ((2001) *J. Org. Chem.* 66(3):697-706) teach a small library of epoxy peptidomimetics as time-dependent reversible inhibitors of cysteine proteases.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotometers, calorimeters, and fluorimeters, and devices that measure the decay of radioisotopes. It is contemplated that any suitable assay can be used in such screening assays. For example, activity of UBP43 can be assessed with a purified peptide substrate or full-length ISG15.

As indicated, selective agents of this invention find application in methods for enhancing pro-apoptotic and degradative pathways of neoplastic or pre-neoplastic cells and preventing or treating cancer, in particular cancers such as APL or lung cancer. Generally, such methods involve administering to a subject in need of treatment an agent that selectively activates the expression or activity of UBE1L or ISG15, or selectively inhibits the expression or activity of UBP43 in an amount that effectively reduces the expression of cyclin D1 or cancer cell proliferation by at least 60%, 70%, 80%, 90%, 95%, 99% or 100%. Subjects benefiting from treatment with an agent of the invention include subjects confirmed as having cancer, subjects suspected of having cancer, or subjects at risk of having cancer (e.g., subjects with a family history or having been exposed to cancer-causing agents). In the context of this invention, a subject can be any mammal including human, companion animals (e.g., dogs or cats), livestock (e.g., cows, sheep, pigs, or horses), or zoological animals (e.g., monkeys). In particular embodiments, the subject is a human.

While certain embodiments of this invention embrace in vivo applications, in vitro use of agents of the invention are also contemplated for examining the effects of UBE1L and/or ISG15 activation or UBP43 inhibition on particular cells, tissues or regions. In addition to treatment, agents of the invention also find application in monitoring the phenotypic consequences of enhancing pro-apoptotic and degradative pathways of neoplastic or pre-neoplastic cells in rodent models of cancer.

Agents of the present invention are preferably administered in the form of a pharmaceutical composition which includes the agent in admixture with a pharmaceutically acceptable vehicle. Desirably, the pharmaceutically acceptable vehicle is selected routinely by those of skill in the art based upon the type of cancer being treated and the route of administration best suited for treatment of that type of cancer. Effective amounts of the agent to be administered can be determined routinely by those of skill in the art based upon in vitro and in vivo assays demonstrative of pharmacological activity such as those described herein.

The invention is described in greater detail by the following non-limiting examples.

EXAMPLE 1

Materials and Methods

Cell Culture and Induction Protocol. RA and dimethyl sulfoxide (DMSO) were purchased from Sigma Chemical Company (St. Louis, Mo.). Stock RA (10 mM) solutions were dissolved in DMSO, stored in liquid nitrogen, and used in the dark during experiments. RPMI-1640 and DMEM were purchased from Cellgro/Mediatech (Herndon, Va.).

The NB4 APL cell line expresses PML/RARα (Lanotte, et al. (1991) *Blood* 77:1080-1086). NB4-S1 and NB4-R1 are RA-sensitive and RA-resistant clones of NB4 cells, respectively (Nason-Burchanel, et al. (1997) *Differentiation* 61:321-331). These cells were cultured in RPMI-1640 medium supplemented with 10% FBS (see, Nason-Burchenal et al. (1997) supra).

Chinese hamster ovary (CHO) cells were cultured in DMEM supplemented with 5% FBS, 100 units/ml penicillin, 100 units/ml streptomycin, and 2 mM L-glutamine in a 5% $CO_2$ humidified incubator at 37° C.

Human bronchial epithelial cells (BEAS-2B) were cultured in serum-free LHC-9 medium (Biofluids, Rockville, Md.) in accordance with established techniques (Langenfeld, et al. (1997) *Proc. Natl. Acad. Sci. USA* 94:12070-12074; Boyle, et al. (1999) *J. Natl. Cancer Inst.* 91:373-379).

HeLa cells were cultured in DMEM supplemented with 10% FBS, 100 units/ml penicillin, 100 units/ml streptomycin, and 2 mM L-glutamine in a 5% $CO_2$, humidified incubator at 37° C.

The H358 lung cancer cell line was cultured in RPMI-1640 medium (INVITROGEN Corporation, Carlsbad, Calif.) containing L-glutamine, 10% fetal bovine serum and 1% antibiotic-antimycotic solution (CELLGRO, Herndon, Va.) (Petty, et al. (2004) *Clin. Cancer Res.* 10:7547-54). Cells were incubated at 37° C. in a humidified incubator with 5% $CO_2$. Bexarotene treatments of HBE and lung cancer cells were accomplished according to known methods (Dragnev, et al. (2007) *Clin. Cancer Res.* 13:1794-800; Dragnev, et al. (2005) *J. Clin. Oncol.* 23:8757-64).

Differentiation and Apoptosis Markers. NB4 cell differentiation was scored by using the nitroblue tetrazolium (NBT) reduction assay (Nason-Burchenal, et al. (1997) supra; Nason-Burchenal, et al. (1998a) *Blood* 92:1758-1767; Nason-Burchanel, et al. (1998b) *Oncogene* 17:1759-1768) Transductants were identified by green fluorescent protein (GFP) coexpression. Apoptosis was scored by using established techniques and Hoechst staining of transductants that co-expressed GFP (Nason-Burchenal, et al. (1998a) supra; Nason-Burchenal, et al. (1998b) supra; Stadheim, et al. (2001) *Cancer Res.* 61:1533-1540). Digital images were collected using an OLYMPUS 1X70 inverted microscope, a cooled charge-coupled device camera, and a MIRACAL Pro Single Cell Imaging System (OLYMPUS LSR Research, Melville, N.Y.).

Plasmid Constructs and Transient Transfection. A full length UBE1L cDNA containing plasmid was obtained in accordance with the method of Kote, et al. ((1995) *Gene Expression* 4:163-175). The pGEM-HA-1E1 plasmid was obtained in accordance with the method of Handley et al. ((1991) *Proc. Natl. Acad. Sci. USA* 88:250-262). pSG5-HA-1E1 was constructed by cloning the HA-1E1 fragmented into the pSG5 expression vector. An EcoRI fragment containing the UBE1L cDNA was cloned into EcoRI-restricted pSG5 to yield the pSG5-UBE1L plasmid. A truncated UBE1L plasmid (UBE1L-T) lacked an EclXI/SnaBI fragment in the carboxy terminus of UBE1L. The hemagglutinin (HA)-tagged PML/RARα expression vector was constructed from pCMX-PML/RARα and pCMV-HA (CLONTECH) plasmids. The pGL3-UBE1L Luc reporter plasmid contained the luciferase gene and 51 promoter elements of UBE1L. It was constructed by using a PCR-amplified fragment of the UBE1L promoter derived from NB4-S1 genomic DNA (forward primer, 5'-GCA ACC GAG TGA GAC TGT CT-3', SEQ ID NO:4; reverse primer, 5'-GCG CTC AGA GAT AGG GTT T-3', SEQ ID NO:5). DNA sequence analysis confirmed this cloning.

The pcDNA3-UbCH8 plasmid is known in the art (Zhao, et al. (2005) *Proc. Natl. Acad. Sci. USA.* 102(29):10200-10205). His6-tagged pcDNA3-ISG15 and pcDNA3-His-UBP43 expression vectors are also known in the art (Pitha-Rowe, et al. (2004) *J. Biol. Chem.* 279: 18178-87; Liu, et al. (2003) *J. Biol. Chem.* 278:1594-602; Shah, et al. (2008) *Mol. Cancer. Ther.* 7:905-14). The HA-tagged pRcCMV-cyclin D1 plasmid is known in the art (Rao, et al. (1994) *Mol Cell Biol.* 14:5259-5267). The lysine-less HA-tagged cyclin D1 species was previously described (Feng, et al. (2007) *Oncogene* 26:5098-106). Transient transfection of BEAS-2B cells was accomplished using EFFECTENE transfection reagent (QIAGEN, Valencia, Calif.) and optimized methods (Feng, et al. (2007) supra). Transfections of pSG5-UBE1L, insertless pSG5 vector or with small interfering RNAs (siRNAs) were accomplished using established techniques (Pitha-Rowe, et al. (2004) *Cancer Res.* 64:8109-15; Shah, et al. (2008) supra). Transient transfection of BEAS-2B or CHO cells was accomplished by using EFFECTENE and transfection methods in accordance with the manufacturer's instructions (Qiagen, Valencia, Calif.). A β-galactosidase reporter plasmid (pCH111) was cotransfected to control for transfection efficiencies.

SiRNAs targeting UBE1L or a RISC-free control siRNA were synthesized (Dharmacon, Lafayette, Colo.). Different siRNAs were designed to target UBE1L: UBE1L siRNA1 (5'-CGA CAA CTT TCT CCC GTT A-3', SEQ ID NO:6) and siRNA2 (5'-CCT CGG AGT TAG GGC GAA T-3', SEQ ID NO:7). Transfection efficiency was monitored by transfecting SIGLO Green Transfection Indicator (Dharmacon). Percent of cells transfected was assayed by flow cytometry.

UBE1L mRNA Expression Assays. UBE1L mRNA expression was assessed by a reverse transcription-PCR assay in accordance with established methods (Kakizuka et al. (1991) *Cell* 68:663-674). The forward primer was 5'-AGG TGG CCA AGA ACT TGG TT-3' (SEQ ID NO:8), and the reverse primer was 5'-CAC CAC CTG GAA GTC CAA CA-3' (SEQ ID NO:9). The PCR product was visualized by probing with a $^{32}$P-labeled primer. Results were confirmed independently by Northern analysis using a 1.0-kb EcoRI/NcoI-radiolabeled UBE1L probe in accordance with standard techniques (Langenfeld et al. (1997) *Proc. Natl. Acad. Sci. USA* 94:12070-12074). This probe had limited homology to E1.

Generation of Anti-UBE1L Antisera. Two rabbit polyclonal antibodies against UBE1L were independently derived (Covance Research Products, Denver, Pa.) using one peptide within the amino terminus (Asp-Cys-Asp-Pro-Arg-Ser-Ile-His-Val-Arg-Glu-Asp-Gly-Ser-Leu-Glu-Ile-Gly-Asp (SEQ ID NO:10)) and a second peptide within the carboxyl terminus (Pro-Gly-Ser-Gln-Asp-Trp-Thr-Ala-Leu-Arg-Glu-Leu-Leu-Lys-Leu-Leu (SEQ ID NO:11)). Specificities of these antisera were confirmed by immunoblot analyses of UBE1L-transfected CHO cells.

Immunoblot Analysis. Immunoblot analyses were performed using established techniques (Langenfeld, et al. (1997) *Proc. Natl. Acad. Sci. USA* 94:12070-12074; Spinella, et al. (1999) *J. Biol. Chem.* 274:22013-22018). Anti-RARα antibody was provided by and can be purchased from P. Chambon (Institut National de la Sant et de la Recherche Mdicale, Strasbourg, France) to detect PML/RARα (Nason-Burchenal, et al. (1998) *Blood* 92:1758-1767; Nason-Burchenal, et al. (1998) *Oncogene* 17:1759-1768). An anti-HA mAb was purchased (Babco, Richmond, Calif.) as was an anti-actin polyclonal antibody, C-11 (Santa Cruz Biotechnology, Santa Cruz, Calif.).

Cells were lysed with ice-cold radioimmunoprecipitation (RIPA) lysis buffer, using established techniques (Pitha-Rowe, et al. (2004) supra; Pitha-Rowe, et al. (2004) supra; Feng, et al. (2007) supra; Ma, et al. (2005) *Cancer Res.* 65:6476-83). Lysates were size-fractionated by sodium dodecyl sulphate-polyacrylamide gel electrophoresis (SDS-PAGE) assays before transfer to nitrocellulose membranes (Schleicher & Schuell Bioscience, Inc., Keene, N.H.). The polyclonal antibody recognizing the UBE1L amino terminus of UBE1L was used for immunoblot and immunohistochemical assays. Other primary antibodies for immunoblot assays included a rabbit polyclonal antibody recognizing cyclin D1 (M-20) (Santa Cruz Biotechnology, Santa Cruz, Calif.), a murine monoclonal antibody against hemagglutinin (HA)-tagged proteins (Babco, Richmond, Calif.) and a goat polyclonal antibody recognizing actin (Santa Cruz Biotechnology). Anti-mouse and anti-rabbit antisera were purchased (Amersham Biosciences, Piscataway, N.J.) as was anti-goat antisera (Santa Cruz Biotechnology) and these were used as respective secondary antibodies. Membranes used for immunoblot analyses were treated with the MEMCODE reversible stain (Pierce, Rockford, Ill.). Treatment with the proteasome inhibitor ALLN was used (Ma, et al. (2005) supra). Quantification of signal intensities was scored as before (Shah, et al. (2008) supra; Feng, et al. (2007) supra; Ma, et al. (2005) supra). To assess cyclin D1 protein stability following UBE1L transfection, cells were treated with or without CHX (40 µg/ml) (Feng, et al. (2007) supra).

Retroviral Constructs and Transduction Procedures. MSCV-IRES-GFP was constructed to express UBE1L cDNA by cloning an EcoRI fragment from pSG5-UBE1L into an EcoRI site of this retroviral vector. Restriction endonuclease and partial DNA sequence analyses confirmed cloning was in the desired orientation. A vector without an insert served as a control. For each vector, 10 µg was transiently transfected using calcium phosphate precipitation along with the CELLPHECT Transfection kit (Amersham Pharmacia, Piscataway, N.J.). The 293GPG packaging cell line was obtained from Harvard University (Cambridge, Mass.) and is available to other investigators. Forty-eight hours later viral supernatant from 293GPG transfectants (Ory, et al. (1996) *Proc. Natl. Acad. Sci. USA* 93:11400-11406) was used to transduce NB4-S1 or HeLa cells in the presence of 6 µg/ml POLYBRENE (Sigma Chemical Company, St. Louis, Mo.). Twenty-four hours later, FACS analysis was performed, and cells positive for GFP expression were harvested by sorting and used for these experiments.

Five µg of MSCVIRES-UBE1L-GFP and an empty vector were independently transfected into the Phoenix Amphotropic packaging cell line (ATCC, Manassas, Va.) using FUGENE 6 (Roche, Indianapolis, Ind.), and the vendor's recommended procedures. Forty-eight hours later, viral supernatants were harvested from respective transduced BEAS-2B HBE or H358 lung cancer cells with 4 µg/ml POLYBRENE (Sigma). Forty-eight hours later, cells positive for GFP expression were harvested using a FACSTAR Plus (Becton Dickinson, San Jose, Calif.) high speed sorting cytometer. This was repeated one week later to enrich for studied transductants.

Immunoprecipitation and Pull-Down Assays. After BEAS-2B cells were transiently transfected with indicated expression vectors, transfectants were lysed with RIPA buffer for immunoprecipitation or for Ni-NTA-agarose (INVITROGEN) pulldown using optimized procedures (Shah, et al. (2008) supra). Anti-HA antibody (Santa Cruz Biotechnology) and protein A/G beads (Santa Cruz Biotechnology) were used. Ni-NTA-agarose pull-down assays were performed according to conventional methods (see, e.g., Shah, et al. (2008) supra).

Translational Research Studies. Paraffin-embedded and formalin-fixed tissues were obtained from an Institutional Review Board-approved proof of principle bexarotene lung cancer trial (Dragnev, et al. (2007) supra). Tissues were examined for cyclin D1 (Petty, et al. (2004) supra; Dragnev, et al. (2007) supra; Dragnev, et al. (2005) supra), UBE1L (Pitha-Rowe, et al. (2004) supra), ISG15 (Andersen, et al. (2006) *Br. J. Cancer* 94:1465-71), and Ki-67 (Petty, et al. (2004) supra; Dragnev, et al. (2007) supra; Dragnev, et al. (2005) supra) immunohistochemical expression profiles.

Clonal Growth Assays. Clonal growth assays (Langenfeld, et al. (1996) *Oncogene* 13:1983-90) were performed using $5\times10^2$ BEAS-2B and $1\times10^3$ H358 cells. These cells were independently engineered to over-express UBE1L or a control vector. Colonies were treated with bexarotene or vehicle (dimethyl sulfoxide, DMSO) to determine dose-responsive effects. Two weeks later, visible colonies were fixed and stained with DIFF QUIK solution (Baxtor, McGaw Park, Ill.) and quantified with the Col Count instrument (Oxford Optronix, Oxford, UK).

EXAMPLE 2

Role of UBE1L and the UBE1L-Dependent Pathway in APL

All-trans-retinoic acid (RA) treatment induces remissions in acute promyelocytic leukemia (APL) cases expressing the t(15; 17) gene product, promyelocytic leukemia (PML)/retinoic acid receptors (PML/RARα). Microarray analyses have revealed induction of UBE1L (ubiquitin-activating enzyme E1-like) after RA treatment of NB4 APL cells. The kinetics of this induction was studied in RA-sensitive NB4-S1 APL cells using a reverse transcription-PCR assay. UBE1L mRNA induction occurred by three hours after 10 µM RA treatment. These results were independently confirmed by northern analysis and after 1 µM RA treatment by reverse transcription-PCR assay. In contrast, UBE1L expression was not induced during the same time period, despite 10 µM RA treatment of the RA-resistant NB4-R1 cell line. This is indicative of UBE1L being a direct retinoid target.

Further, the direct relationship between UBE1L induction and effective retinoid treatment of APL cells was demonstrated by examination of UBE1L immunoblot expression. For these experiments, immunogenic peptides described herein were used to generate independent polyclonal antisera recognizing the amino or carboxyl termini of UBE1L protein, respectively. Chinese Hamster Ovary (CHO) cells that did not basally express UBE1L mRNA were transfected with a full-length UBE1L cDNA or an insertless vector. CHO cells transfected with UBE1L expressed UBE1L protein. In contrast, cells transfected with an insertless vector did not express this 112-kDa species. The UBE1L immunoblot expression profiles were also compared in RA-sensitive versus RA-resistant NB4 cells. UBE1L protein was basally expressed at low levels in both cell lines. However, protein expression was induced only after RA (1 µM) treatment of NB4-S1 APL cells.

A hallmark of RA response in APL is PML/RARα degradation (Yoshida, et al. (1996) supra; Raelson, et al. (1996) supra; Nervi, et al. (1998) supra; Zhu, et al. (1999)). RA treatment has been reported to repress PML/RARα expression in NB4-S1, but not in RA-resistant NB4-R1 cells (Nason-Burchenal (1997) *Differentiation* 61:321-331). To examine the relationship in APL cells between UBE1L and PML/RARα expression, immunoblot expression profiles for these species were examined before and after 24 hour RA (1 µM) treatment of NB4-S1 cells. An inverse relationship was evident between UBE1L and PML/RARα expression both before and after RA treatment thus indicating a direct role for PML/RARα in regulating UBE1L expression.

A 1.3-kb fragment of the UBE1L promoter was then demonstrated to be capable of mediating transcriptional response to RA in a retinoid receptor-selective manner. PML/RARα, a repressor of RA target genes, abolished this UBE1L promoter activity. To examine the potential for PML/RARα to affect UBE1L, 1.3 kilobases (kb) of the UBE1L promoter upstream of the ATG translation start site was cloned into a luciferase-containing reporter plasmid. This reporter plasmid was transfected into CHO cells in the presence and absence of RA treatment. This fragment of the UBE1L promoter was capable of mediating transcriptional response to RA in a retinoid receptor-selective manner.

The relationship between PML/RARα and activity of this UBE1L reporter plasmid was examined when PML/RARα was cotransfected with this reporter plasmid. Cotransfection of PML/RARα with RARE led to a marked repression of UBE1L reporter activity before and after RA (1 µM) treatment. This inhibition depended on the dosage of transfected PML/RARα. In each experiment, a cotransfected β-galactosidase reporter plasmid was used to control for transfection efficiencies. No appreciable effect of PML/RARα on the transcriptional activity of the β-galactosidase reporter plasmid was observed. Thus, PML/RARα repressed activity of this UBE1L reporter plasmid.

UBE1L has homology to E1. However, E1 mRNA was not induced after RA (1 µM) treatment of NB4-S1 cells, thus indicating different effects of RA on expression of UBE1L and E1.

A hallmark of RA response in APL is PML/RARα degradation. Accordingly, the ability of UBE1L as well as E1 to trigger PML/RARα degradation was next examined. Cotransfection assays were performed using cells that do not express PML/RARα. In these experiments CHO cells that did not express UBE1L and BEAS-2B cells that expressed low levels of UBE1L, but could be readily transfected with RARs or PML/RARα, were used. Degradation of transfected PML/RARα was triggered by UBE1L in a dose-dependent manner after transfection of CHO cells or BEAS-2B cells. This degradation of PML/RARα occurred in the absence of RA treatment. The PML domain of PML/RARα appeared to be more sensitive to degradation by UBE1L than the RARE domain. Transfection of a truncated UBE1L (pSG5-UBE1L-T) did not cause PML/RARα degradation. To establish that PML/RARα degradation was a distinct UBE1L function, E1 was also transfected into BEAS-2B cells with PML/RARα E1 did not cause PML/RARα degradation. Thus, transfection of UBE1L, but not E1, led to PML/RARα degradation even without RA treatment.

The effects of engineered overexpression of UBE1L in APL cells on growth or differentiation state of these cells was then examined. To overexpress UBE1L in APL cells, retroviral vectors (Ory, et al. (1996) supra) were constructed to express UBE1L or no insert. Coexpressed GFP was used to enrich for retroviral-expressing cells after FACS sorting. HeLa cells, which do not express PML/RARα and basally express UBE1L at low levels, were used as a control for these experiments because retroviral transduction conditions were previously optimized in these cells. UBE1L overexpression was engineered independently in NB4-S1 and HeLa cells using the described retroviral transduction method. As a control, an insertless control vector was independently introduced into these cell lines as confirmed by immunoblot analysis. A striking difference in biological effects was observed after transduction of UBE1L into NB4-S1 versus HeLa cells. UBE1L overexpression in NB4-S1 cells resulted in the rapid induction of apoptosis as measured by the Hoechst staining of transduced cells. Three independent fields were examined for the insertless control NB4-S1 transfectants and 5.1% of these cells were apoptotic. Analysis of UBE1L-transduced NB4-S1 cells revealed a high proportion (39.7%) of apoptotic cells. These transductants did not exhibit morphological evidence of leukemic cell maturation. This lack of induced differentiation was confirmed by the absence of NET-positive cells (see Table 1).

TABLE 1

| Cell line | NBT, % |
|---|---|
| NB4-S1 (−RA) | 0 |
| NB4-S1 (+RA) | 92 |
| NB4-S1 (−UBE1L) | 0 |
| NB4-S1 (+UBE1L) | 0 |

NBT maturation assays performed on NB4-S1 APL cells after 5 days treatment with RA (1 µM) [designated +RA] or vehicle (DMSO [designated −RA] or transduction of the UBE1L retrovirus, [designated +UBE1L] as compared to transduction of the same retrovirus without an insert (designated −UBE1L].

Promotion of apoptosis was not observed in HeLa cells transduced with either the UBE1L or insertless retroviral vector. Thus, UBE1L transduction preferentially triggered apoptosis in PML/RARα-expressing cells. Induction of apoptosis was so rapid, however, that examination of the mechanisms signaling apoptosis was precluded.

As demonstrated herein, there is a tight link between UBE1L induction and PML/RARα degradation. More specifically, experiments described herein are demonstrative of an antagonistic relationship between UBE1L and PML/RARα. Further, increases in expression of UBE1L rapidly induce apoptosis in cells expressing PML/RARα. Accordingly, UBE1L is believed to be a target for repression by PML/RARα and induction of apoptosis in cells expressing this oncogenic protein.

Additional experiments in BEAS-2B human bronchial epithelial cells confirmed that co-transfection of UBE1L with transfected cyclin D1 triggers degradation of the oncogenic protein cyclin D1. Thus, the degradation program described herein is active beyond leukemia. In this study β-actin was used as a control to confirm that similar amounts of total protein were added per lane. Prior work has implicated cyclin D1 degradation as a chemopreventive target (Langenfeld, et al. (1997) supra; Boyle, et al. (1999) supra). Thus, these experiments directly implicate UBE1L in cancer chemoprevention. The deconjugase UBP43 is also implicated in the described degradation program in that transfection of UBP43 stabilizes cyclin D1 despite transfection of UDE1L in BEAS-2B human bronchial epithelial cells.

RA also augments the ubiquitin-like protein ISG15 expression in RA-sensitive but not resistant NB4 cells. In addition, RA treatment increases intracellular ISG15 conjugation in retinoid-sensitive NB4 cells. This is indicative of a link between increased ISG15 and UBE1L expression and induction of myeloid differentiation. Consistent with this is that RA treatment increases intracellular ISG15 conjugation in retinoid-sensitive NB4 cells. A physical interaction between UBE1L and ISG15 was established in vivo using a transient co-transfection assay. This interaction was not observed when mutant ISG15 lacking essential C-terminal glycines was examined. Thus, these experiments are indicative of a coordinate regulation of UBE1L and ISG15. PML/RARα degradation was also shown to be inhibited by UBP43 transfection as confirmed by co-transfection experiments with PML/RARα and UBP43 where UBP43 was able to overcome the ability of UBE1L to trigger degradation of PML/RARα. Accordingly, it is contemplated that, like UBE1L, induction of ISG15 or inhibition of UBP43 can also enhance degradation of oncogenic proteins such as PML/RARα and promote apoptosis of cancer cells expressing these oncogenic proteins.

EXAMPLE 3

UBE1L Causes Lung Cancer Growth Suppression by Targeting Cyclin D1

UBE1L is implicated as a molecular pharmacologic target inhibiting cyclin D1. This has provided a mechanism for the tumor suppressive role of UBE1L. To determine whether UBE1L affects cyclin expression, BEAS-2B cells were co-transfected with UBE1L and independently with cyclin D1, cyclin D2, cyclin D3 or cyclin E. Only cyclin D1 was inhibited by UBE1L and actin expression was unaffected.

Immunoblot experiments were conducted following transfection of UBP43, the enzyme leading to ISG15 deconjugation. Dose-dependent effects in BEAS-2B cells of transient UBP43 transfection were observed on cyclin D1 protein. Cyclin D1 expression increased as UBP43 transfection dosage increased. UBE1L transfection inhibited cyclin D1 expression in BEAS-2B cells, but UBP43 co-transfection antagonized this effect (FIG. 1). To establish UBE1L affected cyclin D1 protein stability, UBE1L was co-transfected with HA-tagged cyclin D1 into BEAS-2B cells in the presence and absence of CHX. This analysis revealed that UBE1L reduced exogenous cyclin D1 protein stability following CHX treatment. UBE1L transfection also reduced endogenous cyclin D1 protein, but not cyclin D1 mRNA expression in BEAS-2B cells.

It was contemplated that the ubiquitin-like protein ISG15 would complex with cyclin D1. BEAS-2B cells were transiently transfected with or without cyclin D1 and with or without UBE1L and ISG15 expression vectors. Lysates were subjected to immunoprecipitation before immunoblot analyses. These analyses revealed two major conjugates of cyclin D1 following co-transfection of UBE1L, ISG15 and cyclin D1. Transfection of UbCH8, the E2 enzyme for ISG15ylation (Zhao, et al. (2004) *Proc. Natl. Acad. Sci. USA* 101:7578-82) did not appreciably change this conjugation, indicating endogenous UbCH8 expression was not limiting. Treatment with the proteasome inhibitor ALLN stabilized ISG15ylated species. These ISG15-conjugated cyclin D1 species were reduced by UBP43 co-transfection. Indeed, UBP43 over-expression promoted cell growth, but UBP43 knock-down (by small interfering RNA (siRNA) and by short hairpin RNA (shRNA)-based approaches) repressed growth and induced apoptosis.

To establish UBP43 as a molecular pharmacologic target of general importance in cancer therapy or cancer prevention, unique polyclonal antibodies against, respectively, the amino and the carboxyl termini of UBP43 were developed and used in an immunoblot assay for UBP43 detection. Results revealed abundant UBP43 expression in all cancer cell lines examined (including lung cancer and APL). Findings were extended by use of these antibodies for immunohistochemical assays on paraffin-embedded clinical surgical biopsies that revealed frequent over-expression of UBP43 in human cancers.

Specific lysines in cyclin D1 affect cyclin D1 protein stability (Feng, et al. (2007) supra). Whether a lysine-less cyclin D1 species was resistant to UBE1L-mediated inhibition of cyclin D1 was studied and found. This was an expected outcome since absence of lysine residues prevented ISG15ylation. To confirm this inhibition involved a complex between ISG15 and cyclin D1, transfected lysine-less cyclin D1 was immunoprecipitated with anti-HA or pulled-down with Ni-NTA, respectively, before immunoblotting with an anti-HA antibody. This analysis revealed that UBE1L inhibition of cyclin D1 depended on conjugation to lysine(s) within cyclin D1.

Effects of UBE1L expression on BEAS-2B HBE and H358 lung cancer cell growth were studied. Retroviral UBE1L expression was independently accomplished in BEAS-2B and H358 cells. Exogenous UBE1L reduced endogenous cyclin D1 expression in both transduced cell lines (relative to controls). A limiting dilution clonal growth assay confirmed UBE1L over-expression conferred a marked repression of clonal growth. Similar results were obtained in replicate experiments. BEAS-2B and H358 UBE1L transductants exhibited at least a 50% repression (P<0.001) of clonal growth versus insertless controls. To determine whether knock-down of UBE1L affected cyclin D1 expression, two independent siRNAs targeting UBE1L and a control siRNA were independently transfected into ED-1 murine lung cancer cells, which exhibit high basal UBE1L protein expression. Over 90% of these cells were transiently transfected. Knock-down of UBE1L by these siRNAs increased cyclin D1 immunoblot expression in ED-1 cells.

Figure 2:
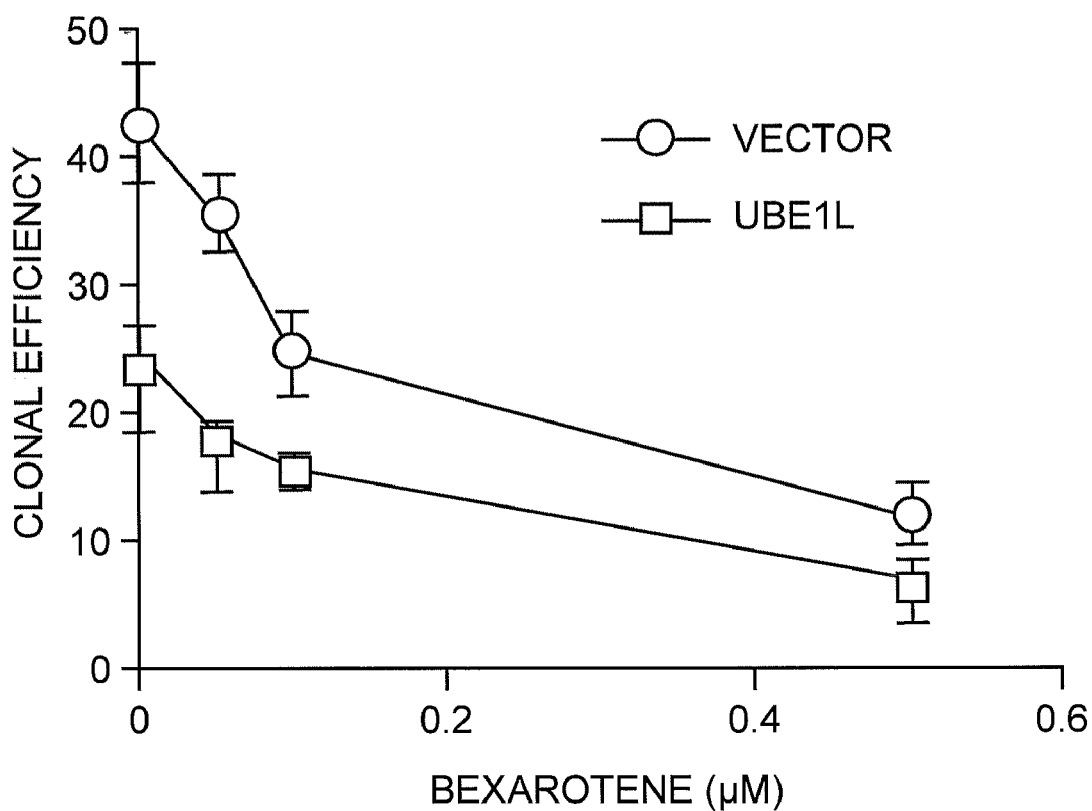
FIG. 2 shows the effects of bexarotene treatment on clonal growth of BEAS-2B human bronchial epithelial cells. Dose-dependent inhibition of BEAS-2B cell growth by bexarotene was found.

Prolonged RA-treatment augments UBE1L expression in BEAS-2B cells (Pitha-Rowe, et al. (2004) *Cancer Res.* 64:8109-15). Studies were undertaken to assess UBE1L expression after treatment of BEAS-2B and H358 cells with bexaratene, a retinoid X receptor agonist. Bexarotene repressed cyclin D1 protein in BEAS-2B and H358 cells. Bexarotene (1 μM) prominently increased UBE1L expression as determined by immunoblot analysis following 10 days treatment of BEAS-2B cells versus vehicle treatment. Similar findings were obtained in H358. Alpha-actin expression served as loading control. Bexarotene treatment also caused a dose-dependent decline of BEAS-2B clonal growth (FIG. 2).

Cyclin D1 immunohistochemical expression declines when high bexarotene levels are measured in lung tumors (Dragnev, et al. (2007) *Clin. Cancer Res.* 13:1794-800). Whether this repression occurred with an increased UBE1L expression in bexarotene post-versus pretreatment lung cancer biopsies was studied. ISG15 immunohistochemical expression was similar in post- and pre-bexarotene treatment biopsies of the lung cancer cases. In contrast, cyclin D1 expression declined in post-versus pre-treatment biopsies when high bexarotene plasma (1.49 μM) and intratumoral (0.31 μM) levels were measured (Dragnev, et al. (2007) supra). Upon further analysis of this case, UBE1L immunohistochemical expression was shown to increase with bexarotene treatment and proliferation decrease in post-versus pretreatment biopsies, as assessed by Ki-67 immunostaining.

Another representative case was examined. This case had low plasma (0.13 μM) and intratumoral (0.09 μM) bexarotene levels (Dragnev, et al. (2007) supra). UBE1L and cyclin D1 immunohistochemical expression profiles were not L appreciably altered by bexarotene treatment. Repression of Ki-67 immunostaining was not observed. A total of five cases were examined with only one having high intratumoral bexarotene levels and also regulation of UBE1L, cyclin D1 and Ki-67 expression. The response rate for UBE1L was 20% (95% CI 1, 72). The odds ratio (OR) assessing association between intratumoral bexarotene concentration and UBE1L increase was 6 (95% asymptotic CI) (0.1, 354.9). This OR indicates a high probability of UBE1L induction in tumors with high bexarotene compared to tumors with low bexarotene levels.

What is claimed is:

1. A method for identifying an agent for use in treating cancer comprising contacting deconjugase UBP43, or a cell expressing the same, with a test agent and measuring the agent's ability to bind UBP43 protein and selectively inhibit UBP43 activity, wherein an agent that selectively inhibits deconjugase UBP43 activity is useful in treating cancer and said cancer is selected from the group consisting of lung cancer, gastric cancer, and breast cancer.

* * * * *

UNITED STATES PATENT AND TRADEMARK OFFICE
CERTIFICATE OF CORRECTION

PATENT NO. : 8,283,113 B2  
APPLICATION NO. : 12/262337  
DATED : October 9, 2012  
INVENTOR(S) : Dmitrovsky et al.

It is certified that error appears in the above-identified patent and that said Letters Patent is hereby corrected as shown below:

On the title page, at item (63) after "Continuation-in-part of application No. 10/506,226, filed on Dec. 29, 2004, now abandoned." please insert:

--which is the U.S. National Stage of PCT/US2003/006905 filed 03/05/2003 which claims the benefit of priority from U.S. Provisional Application Serial Number 60/361,830 filed 03/05/2002.--

Signed and Sealed this  
Seventh Day of May, 2013

Teresa Stanek Rea  
*Acting Director of the United States Patent and Trademark Office*

```
                        SEQUENCE LISTING

<160> NUMBER OF SEQ ID NOS: 11

<210> SEQ ID NO 1
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 1 gatcccagg agaagcattg ttttcaaatt caagagattt gaaaacaatg cttctccttt      60
ttta                                                                 64

<210> SEQ ID NO 2
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 2
agcttaaaaa aggagaagca ttgttttcaa atctcttgaa tttgaaaaca atgcttctcc      60
tggg                                                                 64

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Leu Arg Gly Gly Met His Ile Ser
1               5

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
gcaaccgagt gagactgtct                                                20

<210> SEQ ID NO 5
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 5
gcgctcagag atagggttt                                                 19

<210> SEQ ID NO 6
<211> LENGTH: 19
<212> TYPE: DNA
<213> ORGANISM: Artificial sequence
```

-continued

```
<220> FEATURE:
<223> OTHER INFORMATION: Synthetic oligonucleotide

<400> SEQUENCE: 6
cgacaacttt ctcccgtta                                                19

<210> SEQ ID NO 7
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 7
cctcggagtt agggcgaat                                                19

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
aggtggccaa gaacttggtt                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
caccacctgg aagtccaaca                                               20

<210> SEQ ID NO 10
<211> LENGTH: 19
<212> TYPE: PRT
<213> ORGANISM: Artificial sequence
<220> FEATURE:
<223> OTHER INFORMATION: Synthetic peptide

<400> SEQUENCE: 10

Asp Cys Asp Pro Arg Ser Ile His Val Arg Glu Asp Gly Ser Leu Glu
1               5                   10                  15

Ile Gly Asp

<210> SEQ ID NO 11
<211> LENGTH: 16
<212> TYPE: PRT
<213> ORGANISM: Artificial sequence
<220> FEATURE:
<223> OTHER INFORMATION: Synthetic peptide

<400> SEQUENCE: 11

Pro Gly Ser Gln Asp Trp Thr Ala Leu Arg Glu Leu Leu Lys Leu Leu
1               5                   10                  15
```